United States Patent [19]
Merenkova et al.

[11] Patent Number: 6,022,715
[45] Date of Patent: Feb. 8, 2000

[54] METHOD FOR THE SPECIFIC COUPLING OF THE CAP OF THE 5' END OF AN MRNA FRAGMENT AND PREPARATION OF MRNA AND COMPLETE CDNA

[75] Inventors: Irena Nicolaevna Merenkova; Jean-Baptiste Dumas Milne Edwards, both of Paris, France

[73] Assignee: Genset, S.A., Paris, France

[21] Appl. No.: 08/930,102

[22] PCT Filed: Apr. 29, 1996

[86] PCT No.: PCT/FR96/00651

§ 371 Date: Oct. 31, 1997

§ 102(e) Date: Oct. 31, 1997

[87] PCT Pub. No.: WO96/34981

PCT Pub. Date: Nov. 7, 1996

[30] Foreign Application Priority Data

May 2, 1995 [FR] France ................................ 95 05221
Aug. 3, 1995 [FR] France ................................ 95 09467

[51] Int. Cl.[7] ............................. C12Q 1/68; C12P 19/34; C07H 21/02; C07H 21/00
[52] U.S. Cl. ..................... 435/91.1; 536/231; 536/25.4; 530/350; 530/413; 435/6
[58] Field of Search ............................. 435/6, 91.1, 183; 536/18.7, 23.1, 25.4; 530/350, 413

[56] References Cited

U.S. PATENT DOCUMENTS

| | | | |
|---|---|---|---|
| 4,661,450 | 4/1987 | Kempe et al. | ............ 536/23.7 |
| 5,219,989 | 6/1993 | Sonenberg et al. | ........ 530/350 |
| 5,273,879 | 12/1993 | Goodman et al. | .......... 435/6 |

FOREIGN PATENT DOCUMENTS

| | | |
|---|---|---|
| 0 373 914 A2 | 6/1990 | European Pat. Off. . |
| 0 373 956 A2 | 6/1990 | European Pat. Off. . |
| 0 625 572 A1 | 11/1994 | European Pat. Off. . |

OTHER PUBLICATIONS

Sonenberg et al PNAS vol. 76, No. 9 pp. 4345–4349, 1979.
Sonenberg et al PNAS vol. 175, No. 10 pp. 4843–4847, 1978.
Sonenberg et al PNAS vol. 74, No. 10 pp. 4288–4292, 1977.
Sekine et al Nucleic Acids Symp Ser. No. 29 pp. 143–144, 1993.
Edery et al Mol. Cell. Bio. vol. 15, No. 6, pp. 3363–3371, 1995.
Sarkar et al J. of Bio. Chem. vol. 260, No. 25 pp. 13831–13837, 1985.
Carninci et al Genomics vol. 37 pp. 327–336, 1996.
Carninci et al DNA Research vol. 4, pp. 61–66, 1997.
Lande et al Methods. in Enz. vol 1000 pp. 285–292, 1985.
Bayer et al Methods in Enzymology vol. 184 pp. 139–167, 1990.
Agrawal, et al., "Efficient methods for attaching non–radioactive labels to the 5' ends of synthetic oligodeoxyribonucleotides," *Nucleic Acids Research,* 14(15): 6227–6245 (1986).
Dumas Milne Edwards, "Le clonage de ADNc complets: difficultés et perspectives nouvelles. Apports pur l'étude de la régulation de l'expression de la tryptophane hydrozylase de rat", Thése de Doctorat, Paris 6, pp. 75–88 (1993).
English Translation of Introduction and Conclusion of Dumas Milne Edwards, "Le clonage de ADNc complets: difficultés et perspectives nouvelles. Apports pur l'étude de la régulation de l'expression de la tryptophane hydrozylase de rat", Thése de Doctorat, Paris 6, pp. 75–88 (1993).
Dumas Milne Edwards, et al., "Oligodeoxyribonucleotide ligation to single–stranded cDNAs: a new tool for cloning 5' ends of mRNAs and for constructing cDNA libraries by in vitro amplification", Nuc. Acids Res., 19:5227–5232 (1991).
Zamecnik et al., "Partial Purification of Soluble RNA", Proc. Natl. Acad. Sci., 46:811–822 (1960).
Agrawal et al., *Nuc. Acid. Res.,* 14: 6227–6245 (1986)., "Efficient methods for attaching non–radioactive labels to the 5'ends of synthetic oligodeoxyribonucleotides".

*Primary Examiner*—Kenneth R. Horlick
*Assistant Examiner*—Jeffrey Siew
*Attorney, Agent, or Firm*—Knobbe Martens Olson & Bear

[57] ABSTRACT

The present invention relates to a method for the specific coupling of the cap of the 5' end of a eukaryotic mRNA fragment by a molecule functionalized by an amine functional group. The present invention also provides a method for isolating mRNA 5' end and a method for the preparation of single-stranded cDNA end complementary to the 5' end of mRNA and of double-stranded cDNA corresponding to the mRNA 5' end. The present invention also provides a method for isolating whole-length cDNA corresponding to the entire mRNA.

41 Claims, 7 Drawing Sheets

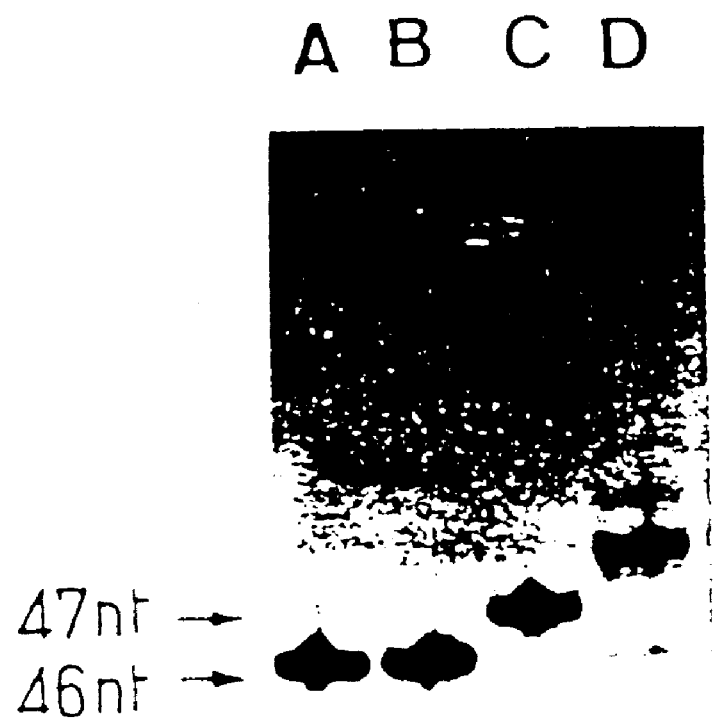
FIG_1

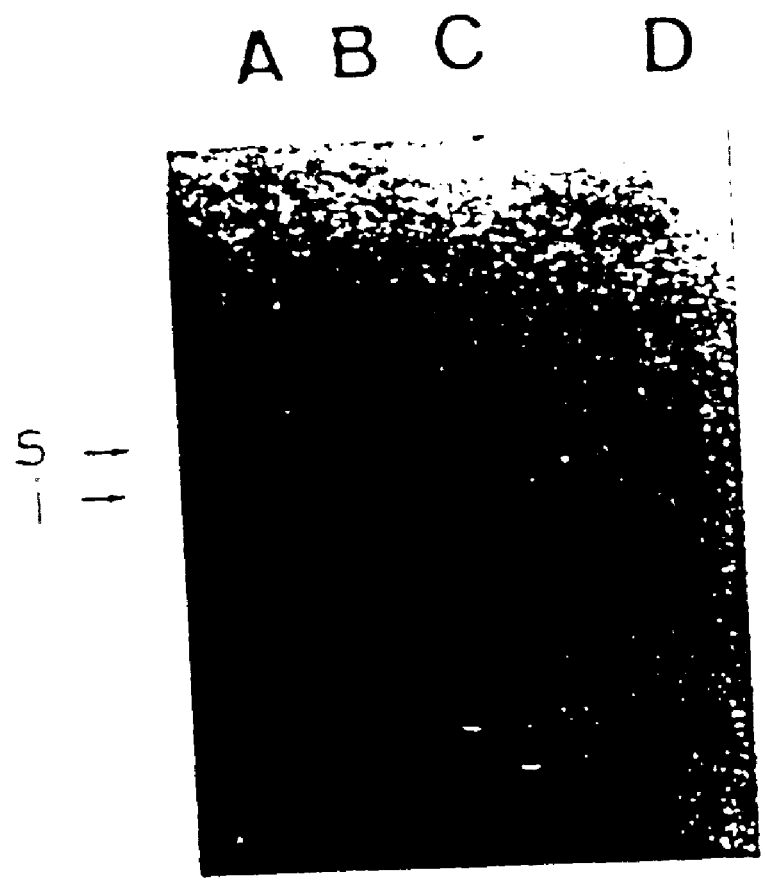
FIG_ 2

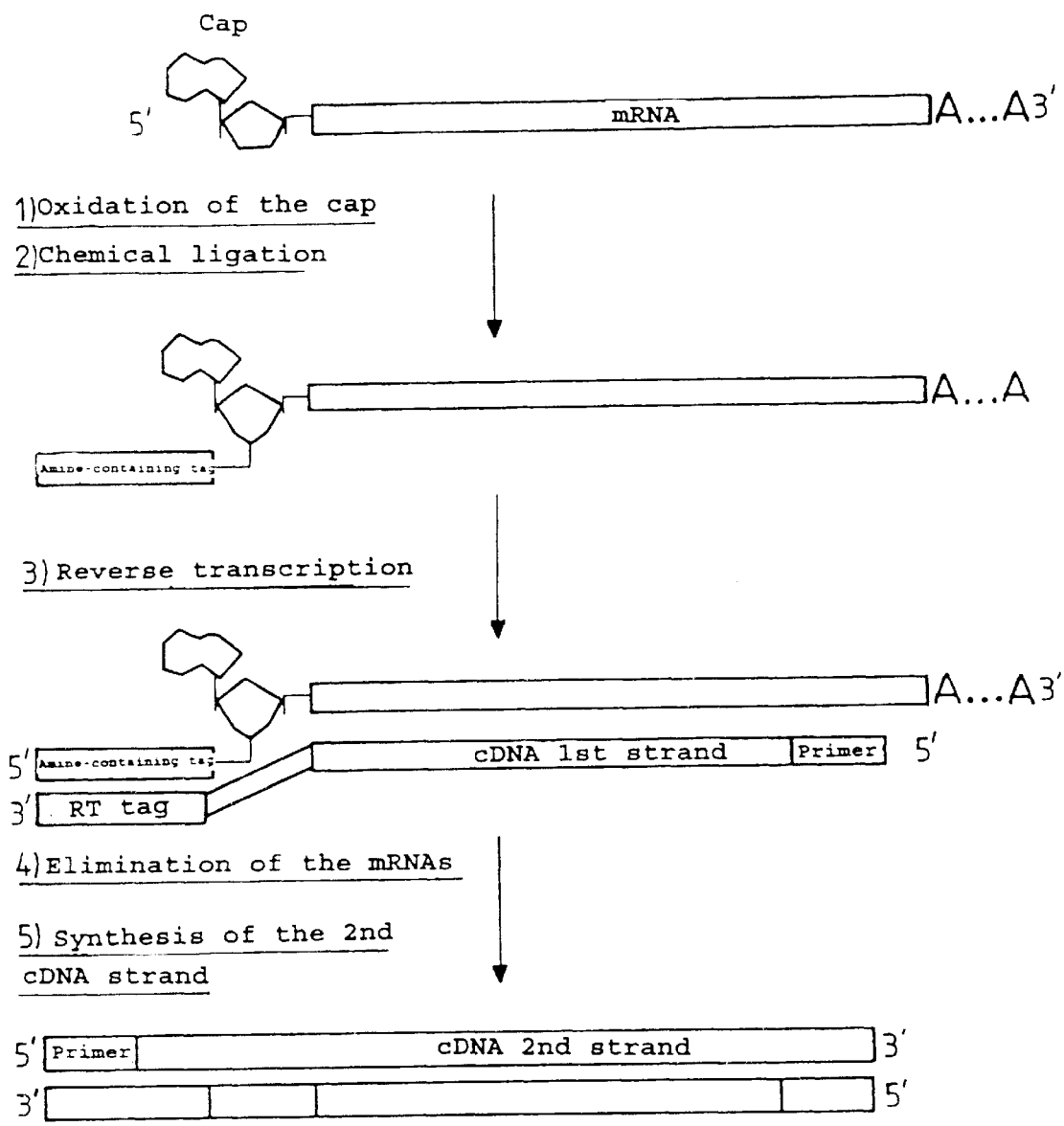

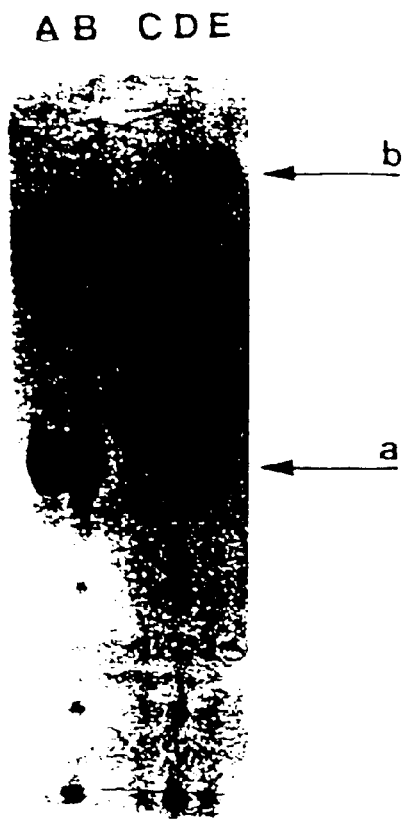
FIG_5
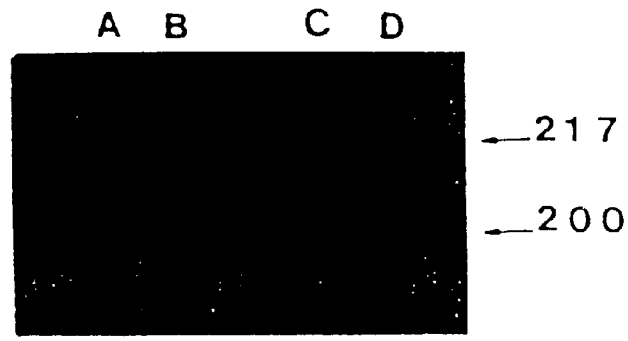
FIG_4

FIG_6
FIG_7

FIG_8
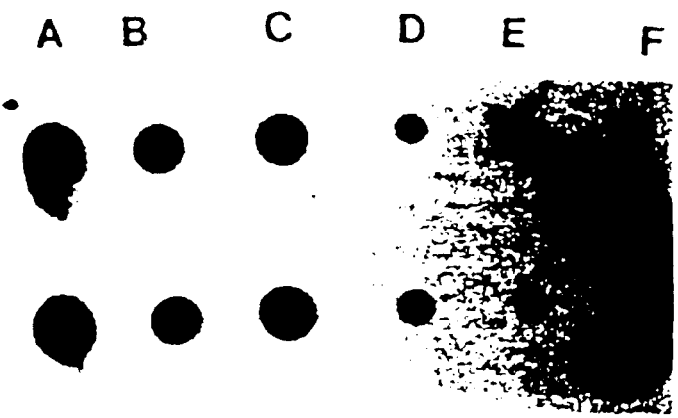
FIG_9

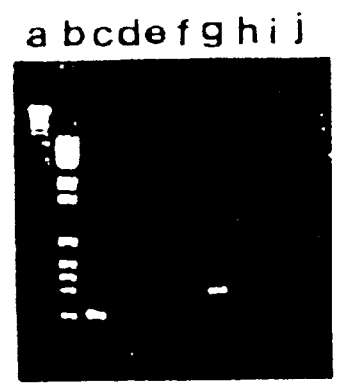
FIG_10
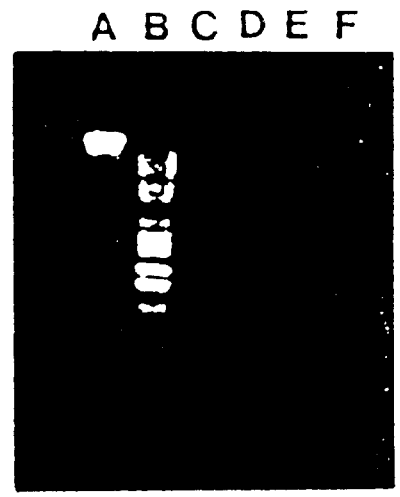
FIG_11

SEQUENCE LISTING (1) GENERAL INFORMATION:

(iii) NUMBER OF SEQUENCES: 18

(2) INFORMATION FOR SEQ ID NO: 1:

(i) SEQUENCE CHARACTERISTICS:
       (A) LENGTH: 65 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 1:

CTTAATACGA CTCACTATAG CATCCTACTC CCATCCAATT CCACCCTAAC TCCTCCCATC    60

TCCAC                                                                65

(2) INFORMATION FOR SEQ ID NO: 2:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 2:

CTTAATACGA CTCACTATAG CAT                                            23

(2) INFORMATION FOR SEQ ID NO: 3:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 3:

GTGGAGATGG GAGGAGTTAG GGTG                                           24

(2) INFORMATION FOR SEQ ID NO: 4:

(i) SEQUENCE CHARACTERISTICS:
       (A) LENGTH: 46 base pairs
       (B) TYPE: nucleic acid
       (C) STRANDEDNESS: single
       (D) TOPOLOGY: linear (ii) MOLECULE TYPE: RNA (genomic)

(ix) FEATURE:
       (A) NAME/KEY: misc_feature
       (B) LOCATION:1
       (D) OTHER INFORMATION:/label= m7Gppp
           /note= "N is m7GpppG"

(xi) SEQUENCE DESCRIPTION: SEQ ID NO: 4:

NCAUCCUACU CCCAUCCAAU UCCACCCUAA CUCCUCCCAU CUCCAC                    46

(2) INFORMATION FOR SEQ ID NO: 5:

(i) SEQUENCE CHARACTERISTICS:

(A) LENGTH: 46 base pairs
         (B) TYPE: nucleic acid
         (C) STRANDEDNESS: single
         (D) TOPOLOGY: linear (ii) MOLECULE TYPE: RNA (genomic)

(ix) FEATURE:
         (A) NAME/KEY: misc_feature
         (B) LOCATION:1
         (D) OTHER INFORMATION:/label= ppp
             /note= "N is pppG"

(xi) SEQUENCE DESCRIPTION: SEQ ID NO: 5:

NCAUCCUACU CCCAUCCAAU UCCACCCUAA CUCCUCCCAU CUCCAC                46

(2) INFORMATION FOR SEQ ID NO: 6:

(i) SEQUENCE CHARACTERISTICS:
         (A) LENGTH: 208 base pairs
         (B) TYPE: nucleic acid
         (C) STRANDEDNESS: single
         (D) TOPOLOGY: linear (ii) MOLECULE TYPE: RNA (genomic)

(ix) FEATURE:
         (A) NAME/KEY: misc_feature
         (B) LOCATION:1
         (D) OTHER INFORMATION:/label= m7Gppp
             /note= "N is m7GpppG"

(xi) SEQUENCE DESCRIPTION: SEQ ID NO: 6:

NCUCCUAUCC CACACUCUCU CACCAUCCUC CACUAUCACC UUUACAUCCA AUCCAAUCCC    60

AAUUACAUAU ACUCAUCCUA ACUCUACCUC UACCCUUCAU UAACUCCAUU UCCAUUCACC    120

UUCUCCAUAC UAACUCCUUC AUACUAUUCA UUUCAUCUCA CCCUCUACCU CACACAUCUC    180

CCACCUUAUC UACCCUAUAC CUCUACUC                                       208

(2) INFORMATION FOR SEQ ID NO: 7:

(i) SEQUENCE CHARACTERISTICS:
         (A) LENGTH: 208 base pairs
         (B) TYPE: nucleic acid
         (C) STRANDEDNESS: single
         (D) TOPOLOGY: linear (ii) MOLECULE TYPE: RNA (genomic)

(ix) FEATURE:
         (A) NAME/KEY: misc_feature
         (B) LOCATION:1
         (D) OTHER INFORMATION:/label= ppp
             /note= "N is pppG"

(xi) SEQUENCE DESCRIPTION: SEQ ID NO: 7:

NCUCCUAUCC CACACUCUCU CACCAUCCUC CACUAUCACC UUUACAUCCA AUCCAAUCCC    60

AAUUACAUAU ACUCAUCCUA ACUCUACCUC UACCCUUCAU UAACUCCAUU UCCAUUCACC    120

UUCUCCAUAC UAACUCCUUC AUACUAUUCA UUUCAUCUCA CCCUCUACCU CACACAUCUC    180

CCACCUUAUC UACCCUAUAC CUCUACUC                                       208

(2) INFORMATION FOR SEQ ID NO: 8:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 8:

ATCAAGAATT CGCACGAGAC CATTA                                                    25

(2) INFORMATION FOR SEQ ID NO: 9:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 9:

TAATGGTCTC GTGCGAATTC TTGAT                                                    25

(2) INFORMATION FOR SEQ ID NO: 10:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 10:

CCGACAAGAC CAACGTCAAG GCCGC                                                    25

(2) INFORMATION FOR SEQ ID NO: 11:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 11:

AGTGATTCCT GCTACTTTGG ATGGC                                                    25

(2) INFORMATION FOR SEQ ID NO: 12:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 12:

AGTGATTCCT GCTACTTTGG ATGGC                                                    25

(2) INFORMATION FOR SEQ ID NO: 13:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 13:

```
GCTTGGTCTT GTTCTGGAGT TTAGA                                               25

(2) INFORMATION FOR SEQ ID NO: 14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

TCCAGAATGG GAGACAAGCC AATTT                                               25

(2) INFORMATION FOR SEQ ID NO: 15:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

AGGGAGGAGG AAACAGCGTG AGTCC                                               25

(2) INFORMATION FOR SEQ ID NO: 16:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

ATGGGAAAGG AAAAGACTCA TATCA                                               25

(2) INFORMATION FOR SEQ ID NO: 17:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

AGCAGCAACA ATCAGGACAG CACAG                                               25

(2) INFORMATION FOR SEQ ID NO: 18:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 18:

GTTAGTGTGG TTGATCT                                                        17
```

METHOD FOR THE SPECIFIC COUPLING OF THE CAP OF THE 5' END OF AN MRNA FRAGMENT AND PREPARATION OF MRNA AND COMPLETE CDNA

The present invention relates to a method for the specific coupling of the cap of the 5' end of eukaryotic messenger RNAs (mRNAs). The present invention also relates to a method for isolating mRNA from eukaryotes comprising the cap at the 5' end. In addition, the present invention relates to a method for the preparation of single-stranded (ss) cDNA complementary to the 5' end of mRNA or of double-stranded (ds) cDNA corresponding to the 5' end of RNA as well as of complete cDNA. The present invention comprises, in addition, reagent kits for carrying out the said methods. The present invention also relates to a method for capturing protein recognizing messenger RNAs. Finally, the present invention also relates to mRNA fragments coupled specifically by the 5' cap to a molecule.

The activity of genes is governed by nucleic domaines situated upstream of the site of initiation of transcription. It is generally accepted that the region of genomic DNA situated within the first 500 nucleotides upstream of the site of initiation of transcription constitute the proximal promoter. The latter contains a large part of the information necessary for regulating transcription. Some sequences facilitating or inhibiting the transcription of genes are indeed situated upstream (5' side) or downstream (3' side) of the proximal promoter. Knowledge of the sequences regulating the activity of genes is crucial for understanding and, in the long term, modifying the mechanisms of expression of genes. The determination of these regulatory domaines is greatly facilitated by the isolation and the characterization of the 5' ends of the messengers. The said ends may indeed be used as point of anchorage in the human genome for the subsequent isolation of the promoters with the aid of conventional molecular biology techniques or alternatively for allowing identification of genes and the location of promoters by computer analysis (homologous sequences) of genomic DNA sequences.

Although the sequence of the 5' ends of mRNAs is of great importance, the conventional techniques used to characterize and isolate specific mRNAs involve the isolation of the corresponding cDNA clones. Now, upon construction, these clones are truncated to a greater or lesser extent in the parts corresponding to the 5' ends of the mRNAs. Definite improvements have recently been made in the isolation and characterization of the 5' ends. Frohman et al. (1) and Delort et al. (2) have described the isolation of the 3' ends of cDNAs corresponding to the 5' ends of mRNAs by means of the addition of a homopolymer to their ends in order to facilitate the cloning of the complete cDNA after amplification by the polymerase chain reaction (PCR). However, the examples of application provided with these methods applied only to relatively abundant messenger RNAs. Delort et al. (2) have shown that the method was difficult to apply to weakly expressed molecular species. The ineffectiveness of the method is due to the addition of homopolymeric sequences to the 3' end of cDNAs through the activity of terminal transferase. Indeed, in this case, the primer used to initiate the synthesis of the second strand (called return primer) and then optionally for the subsequent PCRs necessarily contains a homopolymeric tail at its 3' end. This homopolymeric tail, of sequence anticomplementary to that added to the 3' end of cDNAs can hybridize with internal homopolymeric sequences, thus contributing to the genesis of DNA fragment shorter than the expected fragment. A second factor limiting the sensitivity of the method is linked to the amplification of cDNA fragments synthesized by nonspecific priming. All these cDNA fragments are possible targets for the return primer provided that they have a homopolymeric sequence favourable to the hybridization.

To overcome the disadvantages linked to the addition of a homopolymeric tail, Dumas Milne Edwards et al. (3) ligated to the 3' end of cDNAs a functionalized oligonucleotide (tag) through the activity of $T_4$ phage RNA ligase. The functionalization of the oligonucleotide was aimed at preventing self-ligation of the tags. For that, the oligonucleotide had to have a 5' P end and a 3' end without a hydroxyl functional group. The tagging of single-stranded cDNAs is superior to the addition of a homopolymeric tail because a defined sequence is added to the cDNA molecule. Moreover, the difficulties linked to the use of a primer having a hompolymeric sequence at its 3' end are completely removed. This has considerably improved the isolation of cDNA 3' end. Both strategies described above still have the limitation of starting with cDNA, that is to say with the product of the activity of transcriptase. Now, it is known that the enzyme may have difficulties in recopying the strands of messenger RNA in some regions high in secondary structures for example.

To avoid this difficulty, it has been proposed to directly tag mRNAs (4–7). This second method is based on the addition to the 5' end of mRNAs of a completely or partially ribonucleotide sequence making it possible to both label the 5' end of mRNAs and to provide an anchoring sequence for cloning manipulations. The 5' end of eukaryotic mRNAs is protected by a special chemical structure: the cap (7-methylguanosine linked to the 5' end of messenger RNAs by a 5'-triphosphate bond). In the current state of knowledge, there are no biological means making it possible to directly add a ribonucleotide sequence to the mRNA cap. Moreover, to isolate RNAs using this method, it is necessary to first remove the cap from the mRNAs and then to add the chosen ribonucleotide sequence. This method has the advantage of specifically labelling the RNAs at their 5' end with the aid of a known sequence which may be used as target for specific primers which can be used to synthesize the second cDNA strands and possibly to carry out PCRs. However, the manipulations carried out on RNAs, in particular the number of enzymatic reactions to be carried out limit the use which can be made of this method to large quantities of mRNA. This method has the disadvantage of requiring numerous enzymatic steps which may be limiting because the enzymes may be contaminated with RNases, and between each step the manipulations making it possible to purify the nucleic acids are expensive in material.

There has finally been described a process for purifying mRNA (8) in which there are used the properties of a particular protein to recognize and bind to the cap of the 5' end of mRNAs after selection of cDNA-mRNA heteroduplexes. This method involves, indeed, the prior formation of mRNA-cDNA heteroduplexes and can therefore only apply to mRNAs of linear configuration or denatured beforehand. However, under the denaturing conditions necessary for the linearization of the RNA molecule to promote the attachment of the cap, the said protein described in this process is also denatured and loses its recognition and affinity properties. None of the methods described up until now therefore allows the isolation of complete messenger RNAs.

One aim of the present invention is therefore to provide a method making it possible to isolate complete messenger RNAs and especially their 5' end, which does not have the abovementioned disadvantages.

Another aim of the present invention is to provide a method for the preparation of a 3' end of single-stranded cDNA complementary to the 5' end of mRNAs and of double-stranded cDNA corresponding to the 5' end of mRNAs and especially of complete cDNA.

To do this, the present invention provides, firstly, a method for the specific coupling of the cap of the 5' end of an RNA fragment, especially eukaryotic mRNA, by a molecule functionalized by an amine functional group, which comprises the following steps:

a) the 3' end of the said mRNA fragment is specifically modified such that the last nucleotide no longer comprises an OH group in the 2' and 3' positions;

b) a specific oxidation of diol to dialdehyde is carried out on the 2',3'-cis-diol functional group of the methylguanosine of the 5' end of the said mRNA fragments; and c) the 2',3'-dialdehyde obtained in step b) is coupled with the said amine functional group of the said biological molecule.

"Molecule functionalized by an amine functional group" is understood here to mean a molecule which may naturally comprise an amine functional group or a molecule to which an amine functional group has been added. "Amine functional group" is understood to mean the amine group as such or a functional group comprising a reactive amine group such as hydrazide, carbazide, thiocarbazide or semicarbazide.

The 5' end of messenger RNAs is protected by a particular structure: the cap. The cap is formed of a guanosine methylated in the 7 position and joined to the 5' end of the first base of the RNA by a 5',5'-triphosphate bond. In some cases, the guanosine is methylated in the 2 and 7 positions. Finally, for rare messengers and for numerous small nuclear RNAs, the guanosine is trimethylated in the 2, 7 and 7 positions (9). The sugar (ribose) of this specific nucleoside has a 2',3'-cis-diol functional group. In an mRNA molecule, only the two ends (5' with the cap and 3' with the last sugar 2',3'-OH) have these diols. Accordingly, according to the present invention, to direct the coupling of the biological molecule containing an amine functional group specifically towards the 5' end, the 3' end of the said RNA molecules is specifically modified. According to the present invention, there now remains, in this case, only one diol in 5' which is oxidized to 2',3'-dialdehyde under specific oxidation conditions well known to persons skilled in the art (10, 11). The dialdehyde obtained may then react with numerous reagents containing especially molecules comprising an amine functional group. The coupling of photoactivable molecules (10) and the biotinylation of proteins (12), of oligonucleotides (11) have already been described by reacting a dialdehyde with biotin-hydrazine. The attachment of proteins to the end of hydrazine-containing synthetic oligonucleotides has been described (13). However, the attachment never occurs on the cap in the case of nucleic acids.

In step a), "modification of the 3' end" is understood to mean the substitution, conversion or elimination of the said OH groups of the last base or the elimination or the addition to the 3' end of the said mRNA fragment of one or more nucleotides, such that the last nucleotide of the 3' end no longer contains an OH group in the 2' and/or 3' position of the glycoside ring.

The objective of step a) is to remove the 2',3'-diol functional group from the 3' end such that the specific oxidation of the diol functional group does not occur at the 3' end, but only at the 5' end.

Step a) is optional insofar as some RNA fragments do not comprise a diol in the 2' and 3' positions of the last base of their 3' end.

In one embodiment, the modification of step a) is performed by the addition to the 3' end of the said mRNA fragment of a nucleotide or of an oligonucleotide whose 3' end does not comprise a 2',3'-diol functional group.

The nucleotide or oligonucleotide added may have at its 3' end, for example, at least one OH group in 2' and 3' blocked by a protecting group.

The linkage between the 3' end of the mRNA fragment and the nucleotide or oligonucleotide may be obtained by a 5'-3' internucleotide linkage with the 5' end of the nucleotide or oligonucleotide according to methods known to a person skilled in the art.

In a specific embodiment, a nucleoside diphosphate is ligated in 3' and 5' (pNp), especially by the addition of pCp, using an enzyme, especially RNA ligase and more particularly T4 phage RNA ligase (14–15).

When the mRNA fragment comprises a polyA 3' end ending in 3' with a 2',3'-diol functional group in step a), the specific modification of the 3' end of the said mRNA fragment is carried out by controlled alkaline hydrolysis followed by a step of separating the fragments at the polyA 3' end which are generated by alkaline hydrolysis.

Indeed, the alkaline hydrolysis occurs specifically at the 3' end. It generates several fragments including a first fragment comprising the cap in 5' and the others have a 5' OH end, and their 3' end is of the 3'-phosphate, 2'-phosphate or (2',3')-cyclophosphate type, except one fragment comprising the 3' end of the initial mRNA fragment which should therefore be eliminated.

This elimination can be achieved by any known appropriate means. The mRNA fragments most often comprise a 3' end consisting of a polyA fragment. In this case, it is possible to eliminate the said second fragment, in particular by attachment onto oligo-dT oligonucleotides, especially with the aid of a chromatographic column comprising a solid phase on which oligo-dTs are attached.

The controlled alkaline hydrolysis is advantageously performed in the presence of 0.1 M NaOH at 4° C. for 40–60 minutes.

The oxidation of the α-glycol type diols by periodic acid ($HIO_4$) or by lead tetraacetate specifically causes cleavage of the C—C bond between the two hydroxyl functional groups and the formation of dialdehydes.

In a specific embodiment of step b), the said reagent for the specific oxidation of the diols to dialdehyde is periodate, especially sodium periodate.

In one embodiment of step c), the dialdehyde groups formed by oxidation react mainly with the amine functional groups, under acidic pH conditions, especially a pH varying between 4 and 6. The bond is then stabilized by reduction with a borohydride such as $NaBH_4$ and preferably a cyanoborohydride such as $NaBH_3CN$, in order to stabilize the hydrazone functional group which then becomes converted to hydrazide.

In an appropriate manner, the said functionalized molecule is a biological molecule. As biological molecule, there may be mentioned in particular proteins such as avidin or antibodies, vitamins or ligand molecules used in ligand/receptor interactions, or alternatively oligonucleotides.

The present invention also provides a method for the specific labelling of the cap of the 5' end of a eukaryotic mRNA fragment, characterized in that a coupling method according to the present invention is used in which the said molecule is a labelling molecule.

"Labelling molecule" is understood here to mean a molecule which can be detected, directly or indirectly, that is to say after binding by covalent coupling or interaction with another molecule and/or a solid phase. "Direct detection" is understood to mean especially the cases where the said molecule itself comprises a detectable element such as a radioactive atom, or the said molecule is coupled to an enzyme which can be detected with the aid of a chromogenic substrate or the said molecule is coupled to a fluorescent molecule. "Indirect detection" is understood to mean especially the case where the said molecule is capable of reacting, physicochemically or by covalent coupling, with another molecule itself comprising a directly detectable element such as a radioactive atom, an enzyme or a fluorescent molecule.

The subject of the present invention is also a method for isolating the 5' end of a eukaryotic mRNA from a biological sample, characterized in that a coupling method according to the present invention is used in which the said molecule is a molecule allowing the isolation of the mRNA fragment to which it is coupled.

"5' end of an mRNA fragment" is understood to mean any fragment which comprises the methylguanosine cap in 5'.

"Molecule allowing the isolation" is understood to mean a molecule allowing the direct or indirect isolation of the mRNA fragment to which it is coupled. By "direct isolation", there may be mentioned the case of precipitation in the case of a protein. By "indirect isolation", there may be mentioned the case where the said molecule is capable of reacting with a solid phase or a second molecule attached to a solid phase.

The subject of the present invention is also a reagent kit useful for carrying out a coupling, labelling or isolation method according to the present invention, characterized in that it comprises:

reagents for modification at the 3' end of the said mRNAs;

reagents for oxidation of the 2',3'-diol functional group at the 5' end to dialdehyde; and reagents for covalent coupling between the dialdehyde and the said amine functional group of the said molecule.

In particular, the said oxidation reagent is sodium periodate.

According to one embodiment, the said reagents for coupling with the said amine functional group comprise an acidic buffer at a pH of between 4 and 6 and a reducing reagent consisting of a borohydride.

According to an advantageous variant, the said reagents for modifying the said 3' end are reagents allowing the coupling of the 3' end of the said mRNA with the 5' end of an oligonucleotide or of a nucleotide not containing a 2',3'-diol functional group at its 3' end.

In particular, the said reagents for modifying the 3' end of the said mRNA consist of a nucleotide 3',5'-diphosphate pNp and of a ligation enzyme RNA ligase, in particular T4 RNA ligase.

The present invention also makes it possible to isolate the 5' end of mRNA and especially complete mRNAs by exploiting the chemical reactivity of the 5' end and the possibility of modifying it chemically specifically for the 5' end, of attaching a molecule to it, especially a biological molecule such as biotin. Subsequently, the RNAs thus labelled may be selected by conventional techniques which make it possible to select them, for example by the use of magnetic beads coupled to streptavidin in the case of biotinylated RNAs. In this case, the invention makes it possible to purify, by capturing on an avidin or streptavidin bead, capped and therefore complete messengers or the 5' ends of complete messengers.

More precisely, the subject of the present invention is therefore moreover a method for isolating complete mRNA especially at the 5' end, from a biological sample, characterized in that:

1) the specific labelling of the cap at the 5' end of mRNA is carried out with a first molecule P1 according to the coupling method of the present invention in order to obtain the conjugate P1-mRNA;

2) the said mRNA labelled with the said first biological molecule (P1-mRNA) is exposed to a second molecule P2 which interacts and binds covalently or noncovalently to the said first molecule so as to form a conjugate or respectively a complex (P2/P1-mRNA);

3) the said conjugate or the said complex P2/P1-mRNA is separated from the sample and, 4) cleavage of the covalent bond or decomplexing is optionally performed in order to recover the labelled mRNA P1-mRNA.

In an appropriate manner, in step 2), the said second molecule becomes attached to a solid phase and, in step 3), the solid phase coated with the said conjugate or complex is separated from the sample.

However, if the said molecules P1 and P2 are proteins, the complex P2/P1 may be recovered for example by precipitation; in this case, the use of a solid phase is not necessary.

In one embodiment, as first (P1) and second molecule (P2), biological molecules are used which interact with each other by a noncovalent type bond. Such pairs are well known. There may be mentioned especially the antigen/antibody pairs such as digoxigenin (DIG)/anti-digoxigenin antibody (anti-DIG) or interactions between biological molecules of biotin/avidin or streptavidin type or alternatively hybridization reactions between complementary nucleic acids.

The attachment of P2 onto the solid phase may be covalent or noncovalent depending on methods known to persons skilled in the art.

In a specific embodiment, P1 is biotin hydrazide and P2 is avidin or streptavidin. In this case, avidin or streptavidin may be separated from the biotin-mRNA conjugate simply by heating to about 95° C. in 2% SDS.

The solid phase may consist of the inner face of the vessel in which the biological sample is present or a component such as beads which are introduced into the said vessel.

The method for isolating mRNA according to the invention may comprise an additional step of cleavage between P1 and the said mRNA in which the said first biological molecule P1 is separated in order to recover the noncoupled mRNA.

The subject of the present invention is also an isolation reagent kit useful for carrying out a method for isolating mRNA 5' end according to the invention, characterized in that it comprises the components of a reagent kit for the specific mRNA coupling of the cap in 5' with a said first biological molecule P1 according to the present invention and a solution of the said second molecule or a solid phase on which a said second biological molecule P2 becomes covalently or noncovalently attached.

The subject of the present invention is also a method for the preparation of single-stranded cDNA 3' end and especially complete cDNA, characterized in that it comprises the following steps:

a) a reverse transcription is carried out of mRNA 5' end and especially of complete mRNA obtained by a method for isolating mRNA 5' end according to the present invention;

b) the single-stranded RNAs and nonhybridized RNA fragments are eliminated in order to obtain a population of cDNA/mRNA heteroduplexes in which the mRNA is an complete mRNA whose 5' cap is coupled specifically by a said first molecule.

c) the said heteroduplexes are captured with the aid of a solid phase coated with the said second biological molecule and, d) a dehybridization of the heteroduplexes is carried out in order to recover the single-stranded cDNA fragments comprising the 3' end and especially the complete single-stranded cDNAs.

Advantageously, in step b), the elimination of the single-stranded RNAs or nonhybridized RNA fragments is carried out by enzymatic treatment with the aid of an enzyme which degrades the single-stranded or nonhybridized RNAs and leaves complete the RNA/DNA heteroduplexes.

In particular, after synthesis of a cDNA, the elimination by T1 RNase or S1 nucleases of the RNA molecules or of the free RNA fragments leads to the production of a population of heteroduplexes containing a capped mRNA molecule. The coupling, especially the biotinylation of the RNA molecule allows its capture by the methods mentioned above and therefore the purification of molecules of cDNA 3' end and especially of complete cDNAs.

The present invention also makes it possible to carry out, via the chemical route, the ligation of a "tag" to the cap of the eukaryotic messenger RNAs for the preparation of double-stranded cDNA, the said tag sequence serving as targets for primers used to synthesize the second cDNA strands. "Tag" is understood here to mean a determined nucleic acid sequence (deoxyribo, ribonucleotide and the like) regardless of the process which made it possible to obtain this sequence. This therefore covers natural or synthetic sequences regardless of the chemistry used to obtain them.

The tagging method according to the invention makes it possible to remove the difficulties linked to the use of enzymes to carry out the tagging of the 5' ends of mRNAs. In the enzymatic route for tagging mRNAs involving the prior elimination of the cap, the ligation reaction is catalysed by an enzyme (T4 RNA ligase) which joins one 3'-OH end to a 5'-P end. Because of this, before "uncapping" the mRNAs, it is necessary to inactivate the 5'-P ends of the noncapped RNAs, thereby adding an enzymatic step (catalysed by a phosphatase such as a bacterial alkaline phosphatase (BAP) or calf intestinal alkaline phosphatase (CIP)). As the method used is based on the reactivity of the cap, in a complex population of RNA, only the capped messenger RNAs are tagged.

The subject of the present invention is therefore also a method for the preparation of eukaryotic double-stranded cDNA corresponding to the mRNA 5' end and especially of complete cDNA in which the following steps are carried out:

a) The coupling of the cap of the 5' end of aeukaryotic mRNA fragment is carried out according to a method of the present invention in which the said functionalized molecule is an oligonucleotide tag comprising an amine functional group at its 3' end, and in which method the first step of modification of the 3' end of the mRNA is optional, b) The reverse transcription is carried out of the ligated mRNA obtained in step a), c) The heteroduplexes obtained in step b) are denatured and the single-stranded RNAs are eliminated in order to obtain the first cDNA, then d) The synthesis of the second is carried out with the aid of DNA polymerase and of a primer whose sequence is anti-complementary to the whole or to part of the oligonucleotide tag sequence.

The possibility of carrying out a reverse transcription through the cap was indeed discovered according to the present invention. This capacity has never been demonstrated before the present invention.

This method makes it possible to obtain double-stranded cDNA comprising the end corresponding to the 5' end of mRNA and especially of complete cDNA corresponding to the complete messenger RNA.

The chemical ligation method of step a) uses the reactivity of the diols; in a capped RNA molecule, the two ends of the mRNA fragment can therefore react. A reaction at the level of the sole cap is possible; for that, it is necessary to block the 3' end of the capped RNAs by eliminating the 3'-OH functional group. However, the ligation of a tag to the 3' end of the mRNAs does not in any way limit the use of the invention as is evident from the diagram of FIG. 3. Indeed, a 3'—3' ligation is involved in this case and, in any case, the primers used to prime the reverse transcription are therefore situated upstream of the nucleotide sequence added. For a better yield, the step of modification of the 3' end of the mRNA with a view to a specific ligation of the tag to the 5' end of the said RNA may be preferred.

During step a) of the process for the preparation of double-stranded cDNA according to the invention, a chemically synthesized oligonucleotide tag is preferably used for the ligation. The synthesis of this oligonucleotide tag is carried out taking into account the fact that it is essential to use an oligonucleotide noncomplementary to the product of primer extension in order to avoid the amplification of allochtonous DNA.

The length of the oligonucleotide tag used in the invention should be sufficient to allow the hybridization of a primer which can be used by DNA polymerase. Preferably, an oligonucleotide with a length equal to at least 10 nucleotides is used. For a better implementation of the invention, it may be preferable to use an oligonucleotide tag having a length sufficient to allow the carrying out of additional steps of amplification. Under these conditions, the length of the oligonucleotide tag is advantageously between 10 and 40 nucleotides. In one embodiment, the amine functional group of the oligonucleotide tag is a hydrazide group at its 3' end.

Another subject of the invention consists in a kit for carrying out the process for the preparation of double-stranded cDNA described above, comprising especially the oligonucleotide tag optionally containing an amine functional group at its 3' end and reagents allowing its ligation to the 5' end of the mRNA.

According to a specific variant of the invention, the kit also comprises primers and enzymes allowing the reverse transcription of the initial RNA template to ss-cDNA and the primers and enzymes allowing the synthesis of the second strand. According to another specific variant of the invention, the kit also comprises the primers and enzymes allowing the amplification of the cloned double-stranded nucleic acid.

The subject of the present invention is also a method for capturing a protein Po recognizing an mRNA in which there is used mRNA obtained by an isolation method according to the present invention, which is exposed to the said protein, then the complex (protein/complete mRNA) is recovered and a decomplexing is carried out in order to recover the said protein.

The said mRNA used may be coupled to the said P1 molecule or may be separated from it. Likewise, the said mRNA or P1-mRNA conjugate may be attached to a solid phase. In particular, the P1-mRNA conjugate may be attached to a solid phase via an interaction with the said P2 molecule which is itself attached to the said solid phase.

This method of capture may apply in particular to at least two biologically important situations:

isolation of proteins involved in the regulation of translation and the stability of messenger RNAs, if the mRNAs are premessenger RNAs, the preparation may be used to capture proteins or complexes (SNURPS) involved in splicing.

Other advantages and characteristics of the present invention will emerge in the light of the detailed exemplary embodiments which will follow.

BRIEF DESCRIPTION OF DRAWINGS

These examples are illustrated by

FIG. 1 which represents the polyacrylamide gel electrophoresis of noncapped oligonucleotides (lanes A and B) and capped oligonucleotides (lanes C and D) labelled by ligation of radioactive $^{32}$P pCp and which have been subjected to the cap biotinylation process described in Example 1 (lanes B and D) or not subjected to this process (lanes A and C).

FIG. 2 shows the results obtained during the recovery of the oligonucleotides biotinylated and captured by magnetic streptavidin beads.

FIG. 3 represents the diagram for the chemical ligation of nucleic acids to the 5' end of mRNAs. After purification of the mRNAs by oligo-dT chromatography, the RNAs, whose 3'-OH end has been optionally blocked, are oxidized in the presence of periodate (step 1). Next, a hydrazine-containing nucleotide tag is ligated to the oxidized RNAs (step 2). Riverse transcription (step 3) is primed (primer) by means of oligo-dT, of hexamers with random sequence or alternatively of primers having a specific sequence. When the reverse transcriptase crosses the cap, it can recopy the tag (RT tag). After elimination of the RNAs (step 4), the synthesis of the second strand of cDNAs (step 5) initiated with a primer chosen to hybridize with the sequence of the retrotranscribed tag (RT tag), leads to the production of double-stranded cDNA containing at least the 5' end of the mRNAs.

FIG. 4 represents an autoradiograph of an electrophoretogram of 8% polyacrylamide gel of oligonucleotides of 200 nucleotides labelled with pCp, capped (lanes C and D) or otherwise (lanes A and B), ligated (lanes B and D) or otherwise (lanes A and C) with a tag.

FIG. 5 represents an autoradiograph of an electrophoretogram of 12% polyacrylamide gel of oligonucleotides of 46 nucleotides labelled with pCp, capped (lanes C, D and E) or otherwise (lanes A and B), ligated (lanes B, D and E) or otherwise (A and C) with a tag.

FIG. 6 represents the autoradiograph of an electrophoretogram on 12% polyacrylamide gel of the RNAs, tagged (C, D) or otherwise (A, B) before (A, C) or after (B, D) reverse transcription.

FIG. 7 represents the autoradiogram of an 8% polyacrylamide gel of oligoribonucleotide of 200 nt radiolabelled in 3' by ligation with $^{32}$pCp. Lane A: oligonucleotide of 200 nt, noncapped, oxidized and ligated with the hydrazine-containing tag. Lane B: oligoribonucleotide of 200 nt, capped, oxidized and ligated with the hydrazine-containing tag.

FIG. 8 represents an autoradiograph of a nylon membrane on which the tagged RNAs and the controls were deposited after hybridization of a radiolabelled probe (by kination: phosphorylation reaction) corresponding to an oligodeoxyribonucleotide of sequence anticomplementary to that of the tag. All the spots are duplicated. Lanes A to D: 0.5, 5, 25 and 50 fmol of tag. Lane E: ⅒th of the tagged mRNAs were deposited in two depositions.

FIG. 9 shows an autoradiograph of a nylon membrane on which single-stranded cDNAs and controls have been deposited after hybridization with an oligodeoxyribonucleotide probe radiolabelled by phosphorylation of its 5' end whose sequence is identical to that of the tag. Lanes A to E represent various concentrations (1 pmol, 100 fmol, 50 fmol, 10 fmol and 1 fmol) of a control oligodeoxyribonucleotide of sequence identical to that of the ligated tag. Lane F: deposition of tagged single-stranded cDNAs.

FIG. 10 represents the photograph of a 1.5% agarose gel, stained with ethidium bromide, of PCR products of reverse transcription (½0th of the products of reverse transcription were used for each PCR reaction).

Lanes A and B: molecular weight markers (describe). Lanes C and D: PCR with the globin primers in the presence of cDNA (lane C) or otherwise (lane D). Lanes E and F: PCR with the dehydrogenase primers in the presence of cDNA (lane E) or otherwise (lane F). Lanes G and H: PCR with the pp15 primers in the presence (lane G) or otherwise (Lane H) of cDNA. Lanes I and J: PCR with the EIE4 primers in the presence (lane I) or otherwise (lane J) of cDNA.

In lanes C, E, G and I, the presence of a band of the expected size indicates the presence of the corresponding sequence in the cDNA population.

FIG. 11 represents the photograph of a 1.5% agarose gel stained with ethidium bromide. Same legend as FIG. 10, but the PCRs were carried out with the anti-sense oligonucleotides of each pair of primers and an oligonucleotide whose sequence corresponds to that of the ligated tag. The amplification products of lanes C and E show that the reverse transcription recopied the RNA molecule and the ligated oligodeoxyribonucleotide tag.

EXAMPLE 1:

Specific labelling of the mRNA 5' cap

1. Ligation of the nucleoside diphosphate pCp to the 3' end of messenger RNA.

1 μg of RNA is incubated in a final reaction medium of 10 μl in the presence of:

a) 5 U of T$_4$ phage RNA ligase in the buffer provided by the manufacturer (Gribco—BRL) and, b) 40 U of RNsase inhibitor: RNasin marketed by the company Promega and, c) 2 μl of $^{32}$pCp Amersham #PB 10208. The incubation may be performed at 37° C. for 2 hours or overnight at 7–8° C.

2. Production of RNA in its capped and noncapped form.

The RNA is obtained by transcription in vitro starting with a double-stranded DNA template carrying the promoter for T7 phage RNA polymerase.

2.1. Production of the double-stranded DNA template.

The double-stranded DNA templates are obtained by PCR in the following manner: an oligonucleotide of sequence 5' CT TAA TAC GAC TCA CTA TAG CAT CCT ACT CCC ATC CAA TTC CAC CCT AAC TCC TCC CAT CTC CAC 3' (SEQ ID NO: 1) (the promoter sequence for T7 phage RNA polymerase is in italics) is amplified using a 5' primer of sequence 5° CT TAA TAC GAC TCA CTA TAG CAT C 3' (SEQ ID NO: 2) and a 3' primer of sequence 5' GTG GAG ATG GGA GTT AGG GTG 3' (SEQ ID NO: 3). Each reaction is carried out in a volume of 100 μl and contains 2 mM MgCl$_2$; 200 μM of each of the dNTPs; 60 pmol of each of the primers; 1 ng of single-stranded DNA template and 2.5 units of Taq DNA polymerase. The amplification conditions are the following: 1 cycle comprising 3 min at 94° C., 30 sec at 53° C. and 30 sec at 72° C.; 25 cycles comprising 1 min at 94° C., 30 sec at 53° C. and 30 sec at 72° C.; 1 cycle with 1 min at 94° C., 30 sec at 53° C. and 5 min at 72° C. The amplification products are then separated by electrophoresis on 10% nondenaturing acrylamide gel and then visualized by UV shadowing. The double-stranded DNA templates are then eluted from the gel, subjected to a phenol extraction and then recovered by alcohol precipitation.

2.2. Synthesis of the capped or noncapped RNA.

The RNA is obtained by in vitro transcription of the double-stranded DNA template using the transcription kit "AmpliScribe T7" (Epicentre Technologies). When the reaction medium comprises the 4 NTPs, the RNA produced is free of cap (it is then equipped with a 5' end of type 5'pppGpNpN . . . ). To obtain the capped RNA, GTP is replaced by an analogue of the cap, m7G(5')ppp(5')G. This compound, recognized by polymerase, is incorporated into the 5' end of the nascent transcript during the step of initiation of transcription. However, it cannot be incorporated during the extension step. Consequently, the DNA serving as template for the synthesis of RNA was defined such that the coding strand has only one cytosine in the +1 position.

3. Oxidation of the cap in 5'

0.1 OD unit of RNA is dissolved: two oligoribonucleotides of 47 and 46 nucleotides including 1 capped (+Cap, 47 nucleotides), and the other noncapped (-Cap, 46 nucleotides) were used.

+Cap:
-m7GpppGCAUCCUACUCCCAUCCAAUUCCACCC UAACUCCUCCCAUCUCCAC (SEQ ID NO: 4)

-Cap: pppGCAUCCUACUCCCAUCCAAUUCCAC-CCUAACUCCUCCCAUCUCCAC (SEQ ID NO: 5) in 9 μl of acetate buffer (0.1 M sodium acetate, pH 5.2) and 3 μl of freshly prepared 0.1 M sodium periodate solution.

The mixture is incubated for 1 hour in the dark. Then, the reaction is stopped by adding 4 μl of 10% ethylene glycol. The product is ethanol-precipitated and dialysed against water.

4. Coupling of the dialdehyde with biotin

The oxidation product obtained in the preceding step is dissolved in 50 μl of sodium acetate at a pH of between 5 and 5.2 and 50 μl of freshly prepared 0.02 M solution of biotin hydrazide in a methoxyethanol/water mixture (1:1) of formula:

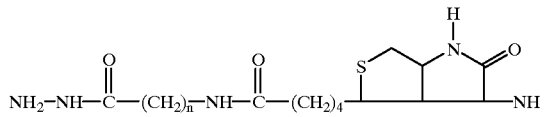

A spacer is used in the biotin hydrazide having n=5. Other commercially available hydrazides may very well be used: with n varying from 0 to 5.

The mixture is then incubated for 2 hours at 37° C. It is precipitated with ethanol and dialysed against distilled water.

EXAMPLE 2:

Capture of labelled mRNA with magnetic beads

1. The streptavidin-coated magnetic beads are prepared according to the manufacturer's instructions (CPG Inc., USA). The RNAs are added to a hybridization buffer (1.5 M NaCl, pH 5-6). Then after incubating for 30 minutes, the unbound and nonbiotinylated material is removed. The beads are washed several times in water with 1% SDS.

2. Recovery of the mRNA

The beads obtained are incubated for 15 minutes at 95° C. in water containing 2% SDS.

3. Experimental results

In both cases, FIGS. 1 and 2, the experimental results presented correspond to autoradiograms of 12% acrylamide gel 0.4 mm thick in TBE buffer.

FIG. 1 shows the results obtained with the oligoribonucleotides of 47 nucleotides whose nucleotide sequences correspond to the sequences given above (Example 1):

Lanes A and B: oligonucleotide of 46 nucleotides free of cap, labelled with radioactive pCp (Example 1, 1.), subjected (B) or not subjected (B) to the procedure described in Example 1, paragraphs 3. and 4. Lanes C and D: oligonucleotide of 47 nucleotides with cap labelled with radioactive pCp, subjected (D) or not subjected (C) to the procedure described in Example 1 (paragraphs 1. to 4.).

The difference in migration observed between lanes A and C is due to the presence of the cap on the oligonucleotides migrating in lane C. The difference in migration observed between lanes C and D is due to the biotinylation of the cap of the oligonucleotides. This demonstrates the specificity of the biotinylation of the cap.

FIG. 2 shows the results obtained during the recovery of the oligonucleotides biotinylated and captured by magnetic streptavidin. The oligonucleotide was labelled with radioactive pCp in 3', then subjected to the procedure described in Example 1.1. Subsequently, the biotinylated oligonucleotides were captured with magnetic beads as described in Example 2, then incubated for 5 (lane A), 15 (lane B) and 30 (lane C) minutes at 95° C. in the presence of 2% SDS.

The products of the reaction were analysed by electrophoresis on 12% polyacrylamide gels under denaturing conditions (7 M urea). The gels were subjected to autoradiography. During this manipulation, the hydrazone bonds were not reduced.

The top bands (arrow s) correspond to the biotinylated RNAs with the hydrazone bond joining the linker of the biotin and of the oligoribonucleotide. The lower bands (arrow i) correspond to the oxidized molecules (oligoribonucleotide). Given that the hydrazone bond has not been stabilized during the heating, it may break and the oligoribonucleotide returns to the dialdehyde form. Lane D presents the oligoribonucleotide labelled with pCp as described in Example 1.1.

EXAMPLE 3:

METHOD FOR THE PREPARATION OF COMPLETE cDNAs. STUDY OF CAPPED OR NONCAPPED SYNTHETIC RNAs

This method comprises the steps of:

A) Labelling the 5' end of the RNAs by a tag

A.1) Oxidation of the diol of the 7-methylguanosine to dialdehyde.

A.2) Functionalization of the 3' end of the tag which should have an NH$_2$ group.

A.3) Chemical ligation of the functionalized tag to the cap.

B) Reverse transcription of the tagged RNAs.

The reverse transcription is primed according to one of the conventional routes consisting in using an oligo-dT primer, a random primer or alternatively a specific primer as in primer extension reactions.

1) Method 1.1. Functionalization of the oligonucleotide tag to be ligated

The nucleic acid phosphorylated in 3' is converted to hydrazide in 3' by treating the nucleic acid with an aqueous solution of hydrazine or of dihydrazide of formula $H_2N(R1)NH_2$ at about 1 to 3 M, and at pH 4.5, in the presence of a carbodiimide type agent soluble in water, for example 1-ethyl-3-(3-dimethylaminopropyl)carbodiimide at a final concentration of 0.3 M at a temperature of 8° C. overnight.

The oligonucleotide is then separated from the other agents and products by a standard technique for isolating oligonucleotides.

1.2. Preparation of the mRNA molecule receiving the tag.

a) Elimination of the 3'-OH functional groups
   by enzymatic ligation of sequences free of 3'-OH, for example ligation of pCp as described in (14);
   by alkaline hydrolysis of the RNAs according to the following procedure in which the alkaline hydrolysis is carried out in a final volume of 100 µl in the presence of 1.5 µg of mRNA in 0.1 N sodium hydroxide for 40 to 60 minutes at 4° C. and then the solution is neutralized with acetic acid and precipitated in ethanol.

b) Oxidation of the diol functional groups.
Up to 1 OD unit of RNA is dissolved in 9 µl of buffer (0.1 M sodium acetate, pH 6–7 or water) and 3 µl of freshly prepared 0.1 M sodium periodate solution.

Allow to incubate for 1 h in the dark.
Stop the reaction by adding 4 µl of 10% ethylene glycol.
Allow to incubate at room temperature for 15 minutes.
Carry out an ethanol precipitation of the product and dialyse against water.

1.3. Chemical ligation.

The RNA is dissolved in an acidic medium, 50 µl of sodium acetate pH 4–6 and 50 µl of solution of functionalized tag, then it is reduced with a borohydride, such that an RNA:tag ratio of 1:20 is obtained.

Allow to incubate for 2 h at 37° C. or overnight (14 h) at 10° C.

Precipitate with ethanol and dialyse against distilled water for the analyses such as acrylamide gel electrophoreses or HPLCs.

1.4. Reverse transcription.

a) synthesis of the first cDNA strand

Materials and reagents

Water bath (90° C. and 40° C.)
Dry ice
Acetylated bovine serum albumin (10 mg/ml (Biolab)
RNasin (5 U/µl, Promega Biotech). The RNasin is provided at the concentration of 40 U/µl; it is diluted to 5 U/µl in an RT buffer
β-Mercaptoethanol (350 mM, Sigma). The β-mercaptoethanol marketed is provided at the concentration of 14.4 M; to obtain a solution of 350 mM, mix 50 µl with 1950 µl of distilled water.
10×RT buffer (100 mM Tris-HCl, pH: 8.3 (42° C.), 80 mM KCl, 16 mM $MgCl_2$)
100 mM solutions of each dNTP (Pharmacia or Boehringer)
1 nM dCTP
20 mM sodium pyrophosphate
$[\alpha\text{-}^{32}P]dCTP$ 400 Ci/mmol (Amersham)

The oligonucleotide used to prime the reverse transcriptase in solution (100 ng/µl in distilled water) in distilled water.

oligo-dT (15–17 (Boehringer))
primers with random sequence
specific primer
Method:
the RNA is diluted in 18 µl of water heated at 95° C., 5 min, then the solution described above in 1.2 is added.
the following components are mixed in a microcentrifuge tube

| | |
|---|---|
| 10 × RT buffer | 2.5 µl |
| BSA (5 1-µl/µl-) | 1 µl |
| RNasin (5 U/µl) | 1 µl |
| dATP (100 mM) | 2 µl |
| dTTP (100 mM) | 0.5 µl |
| dGTP (100 mM) | 0.5 µl |
| dCTP (1 mM) | 2.5 µl | sodium pyrophosphate (200 mM) 1 µl
water to 24 µl
This is mixed with the RNA solution with the hybridized primer, incubated for 45 minutes at 42° C. and, the mixture is stored at −20° C. up to the time of use.

2) Experimental results 2.1. Ligation of oligodeoxyribonucleotides to a 200 mer and a 46 mer RNA.

A) Oligoribonucleotides of 46 or 200 nt are produced in vitro. Depending on the reagents used for their synthesis, these oligoribonucleotides are capped or otherwise (200+, 46+ and 200−, 46− respectively). The sequences of the 46+ and 46− oligonucleotides were given in Example 1, paragraph 3. For the 200 mer, the sequences are the following:
200+:
m7GpppGCUCCUAUCCCACACUCUCUCACCAUCCT CCACUAUCACCLTUUACAUC CAAUCCAAUC-CCAAUACAUAUACUCAUCCUAACUCUAC-CUCUACCCUUCAU UAACUCCAUUUCCAUUCAC-CUUCUCCAUACUAACUCCUUCAUACUAWUCAU U UCAUCUCACCCUCUACCUCACACAUCUC-CCACCUUAUCUACCCUAUACCUCUA CUC (SEQ ID NO: 6)
200−:
pppGCUCCUAUCCCACACUCUCUAC-CAUCCTCCACUAUCACCUIJUACAUCCA AUCCA-AUCCCAAUUACAUAUACUCAUCCUAACU-CUACCUCUACCCUUCAUUA ACUCCAUUUCCAUUCACCUUCUCCAUAC-UAACUCCUUCAUACUAUUCAUUUC AUCUCAC-CCUCUACCUCACACAUCUCCCACCUUAU-CUACCCUAUACCUCUACU C (SEQ ID NO: 7).

After their synthesis, the oligonucleotides are subjected to the procedure described in 1.2.a (ligation to pCp), in order to block their 3'-OH end and then to the procedure described in 1.2.b in order to oxidize the capped oligonucleotides.

B) An oligodeoxyribonucleotide of 17 nt (GTTAGTGTGGTTGATCT) (SEQ ID NO: 13) whose 3 OH end has been modified to 3'-P is subjected to the procedure described in 1.1. in order to add a hydrazide functional group to it in 3'.

C) Subsequently, the oligodeoxyribonucleotide produced in 2.1.B and the oligonucleotides produced in 2.1.A are subjected to ligation as described in 1.3.

FIG. 4: in lanes A and B are represented the results where the noncapped oligoribonucleotides of 200 nt, ligated (lane B) or otherwise (lane A) with a hydrazine-containing oligodeoxyribonucleotide, are deposited. In lanes C and D are deposited the capped oligoribonucleotides of 200 nt, subjected (lane D) or otherwise (lane C) to ligation with a hydrazine-containing oligodeoxyribonucleotide.

This example shows the specificity of the capped RNA tagging reaction. Under the experimental conditions used, 30% of the capped oligoribonucleotide are ligated to the tag.

FIG. 5: in lanes A and B are represented the results where the noncapped oligoribonucleotides of 46 nt, ligated (lane B) or otherwise (lane A) with a hydrazine-containing oligodeoxyribonucleotide, are deposited. In lanes C, D and E are represented the results where the capped oligoribonucleotides, ligated with a hydrazine-containing oligodeoxyribonucleotide (lanes D and E), are deposited. Lane C represents the nonoxidized and nonligated capped oligoribonucleotide. In lanes D and E, the bands at the level of arrow a represent the nonligated, oxidized oligoribonucleotide of 46 nt, the bands at the level of arrow b represent the product of ligation.

This example shows the specificity of the reaction for tagging RNAs capped with another RNA molecular species.

2.2. Reverse transcription of the ligated products.

An oligoribonucleotide of 46 nt is produced in vitro, capped or otherwise. Then, it is subjected to the process of ligation to a tag as described in 1.3, in order to ligate it to a hydrazine-containing oligodeoxy-ribonucleotide of 17 nt.

The ligated oligoribonucleotide (corresponding to bands b of lanes D and E, FIG. 5) and the nonligated oligoribonucleotide (corresponding to bands a of lanes D and E of FIG. 5) were gel-purified. In FIG. 6, lanes A and B represent the nonligated oligoribonucleotide, reverse transcribed (lane B) or otherwise (lane A). Lanes C and D represent the ligated oligonucleotide, reverse transcribed (lane D) or otherwise (lane C).

It can be noted that in both cases, the products are radiolabelled because the 46 mer product is blocked in 3' with radioactive pCp. However, the same quantities of oligonucleotides were deposited in lanes A, B, C and D. The more intense signal in lanes B and D, as well as the presence of an extra band are indicative of reverse transcription taking place.

The signal in lane D indicates that the reverse transcription was carried out through the cap.

EXAMPLE 4:

METHOD FOR THE PREPARATION OF COMPLETE cDNAs (II: STUDY ON PLACENTAL mRNAs)

The method comprises the same steps as in Example 3. We made few modifications in the practical implementation of the method.

1) Method 1.1. Functionalization of the tagged oligonucleotide to be ligated.

3 OD units of the oligodeoxyribonucleotide of sequence ATCAAGAATTCGCACGAGACCATTA (SEQ ID NO: 8) (5'-OH and 3'-P ends) are dissolved in 70 µl of a 1.5 M hydroxybenzotriazole solution, pH 5.3, prepared in dimethylformamide/water (75:25) containing 2 µg of 1-ethyl-3-(3-dimethylaminopropyl)carbodiimide. Incubate for 2 h 30 min at 22° C.

Precipitate twice in $LiClO_4$/acetone.

Resuspend the pellet in 200 µl of 0.25 M hydrazine.

Incubate at 8° C. from 3 to 14 h.

Precipitate twice in $LiClo_4$/acetone.

1.2. Preparation of the molecule receiving the tag.

a) Preparation of the placenta mRNAs

The messenger RNAs were extracted from blocks of placenta of sides 2 cm, stored at −80° C. using conventional techniques of extracting total RNA in acidic phenol and then of oligo-dT chromatography in order to purify the mRNAs. The integrity of the mRNAs is checked by Northern-blotting.

b) Oxidation of the diol functional groups as described in Example 3, paragraph 1.2.

1.3. The chemical ligation was performed as described in Example 3 paragraph 1.3, with the following modification: the precipitation step is replaced by an exclusion chromatography step to remove the nonligated hydrazine-containing oligodeoxyribonucleotides. The procedure followed is the following:

a) Preparation of the column 10 ml of AcA34 (BioSepra#230151) gel are equilibrated in 50 ml of buffer (buffer: 10 mM Tris pH 8.0, 300 mM NaCl, 1 mM EDTA, 0.05% SDS).

The mixture is allowed to sediment. The supernatant is eliminated. The gel is resuspended in 50 ml of buffer.

This step is repeated 2 or 3 times.

A glass bead (diameter 3 mm) is introduced into a 2 ml disposable pipette (length 25 cm).

The pipette is filled with the gel suspension until the height of the gel stabilizes at 1 cm from the top of the pipette.

The column is then equilibrated with 20 ml of equilibration buffer (10 mM Tris HCl pH 7.4, 20 mM NaCl).

b) Chromatography

10 µl of sample (tagged RNA) are mixed in 39 µl of 10 mM urea and 2 µl of blue-glycerol buffer (dissolve 5 mg of bromophenol blue in 60% glycerol (v/v), filter with a filter of diameter 0.45 µm).

The column is loaded. As soon as the sample has penetrated, add equilibration buffer.

100 µl fractions are collected. A tag of 46 nt appears in fraction 16 and the next ones.

Fractions 3 to 15 are preserved; then combined and precipitated with ethanol.

1.4. Reverse transcription

The reverse transcription is carried out with the reverse transcriptase Superscript II from Gibco-BRL, following the manufacturer's instructions. To prime the reaction, 50 pmol of nonamers with random sequence are used.

1.5. Blotting of RNA and of cDNA

The blottings of cDNA and of RNA (RNA and cDNA blots) were carried out on a positively charged nylon membrane according to the methods conventionally used. The cDNAs were deposited on the membrane after the cDNA:RNA heteroduplexes have been subjected to an alkaline hydrolysis in order to eliminate the RNAs.

An oligodeoxyribonucleotide of sequence (TAATGGTCTCGTGCGAATTCTTGAT) (SEQ ID NO: 9) anticomplementary to the ligated oligonucleotide is labelled at its 5' end with $^{32}P$ and hybridized with the RNA blots. An oligonucleotide of sequences identical to that of the ligated oligonucleotide is labelled at its 5' end with $^{32}P$ and hybridized with the cDNA blots.

1.6. Amplification by polymerase chain reaction (PCR)

The cDNAs obtained after reverse transcription are used as template for PCR reaction. Two types of reactions are carried out.

a) Amplifications to detect specific sequences (globin, dehydrogenase, pp15 and elongation factor E4). The following oligodeoxyribonucleotide primers were used.
  alpha-globin
  GLO_S: CCG ACA AGA CCA ACG TCA AGG CCG C (SEQ ID NO: 10)
  GLO_As: TCA CCA GCA GGC AGT GGC TTA GGA G 3' (SEQ ID NO: 11) dehydrogenase
  3 DH_S: AGT GAT TCC TGC TAC TTT GGA TGG C (SEQ ID NO: 12)
  3 DH_As: GCT TGG TCT TGT TCT GGA GTT TAG A (SEQ ID NO: 13) pp15
  PP15_S: TCC AGA ATG GGA GAC AAG CCA ATT T (SEQ ID NO: 14)
  PP15_As: AGG GAG GAG GAA ACA GCG TGA GTC C (SEQ ID NO: 15) Elongation factor E4
  EFA1_S: ATG GGA AAG GAA AAG ACT CAT ATC A (SEQ ID NO: 16)
  EF1A_As: AGC AGC AAC AAT CAG GAC AGC ACA G (SEQ ID NO: 17)

b) Amplifications carried out with antisense (_As) oligodeoxyribonucleotides of the pairs described above and a primer chosen from the sequence of the ligated oligodeoxyribonucleotide (ATCAAGAATTCGCACGAGACCATTA) (SEQ ID NO: 8).

2) Experimental results 2.1. Efficiency of the chemical ligation

The oligonucleotide of 25 nt described in 1.1, Example 4, was modified as described in this paragraph and ligated to the oligoribonucleotide of 200 nt capped or otherwise, described in Example 3.

FIG. 7: Lane A: oligoribonucleotide of 200 nt (radiolabelled at its 3' end with $^{32}$pCp) noncapped, oxidized and ligated to the tag. Lane B: oligoribonucleotide of 200 nt (radiolabelled at its 3' end with $^{32}$pCp) capped, oxidized and ligated to the hydrazine-containing tag. In this lane, the bottom band (i) corresponds to the nonligated 200 mer whereas the top band (s) corresponds to the ligated 200 mer. Under the conditions for preparing the tag and for the ligation, 80% of the capped oligonucleotide were ligated.

2.2. Ligation of the tag with polyA+ RNAs.

Placental messenger RNAs (7 μg) are oxidized under the conditions described in Example 3 and then ligated to a hydrazine-containing oligodeoxyribonucleotide under the conditions described in Example 4. The nonligated oligonucleotide is removed by means of exclusion chromatography (AcA34) as described in point 1.3 of Example 4. The presence of ligated tag is verified by hydridization of a probe with tagged RNA spots on a nylon membrane as described in point 1.5 of Example 4.

FIG. 8 represents an autoradiograph of the membrane after hybridization of the probe. All the spots are duplicated. Lanes A to D: 0.5, 5, 25 and 50 fmol of tag. Lane E: ⅒oth of tagged mRNAs were deposited in two spots.

2.3. Reverse transcription through the cap

⁹⁄₁₀th of the tagged RNAs obtained in point 2.2. of Example 4 are reverse transcribed as described in 1.4., Example 4, and then deposited on a membrane and analysed as described in 1.6., Example 4, or used as template for PCR reactions as described in 1.6. a) and b). FIG. 9 shows an autoradiograph of the membrane after hybridization with the radiolabelled probe described in 1.6.

Lanes A to E represent various concentrations (1 pmol, 100 fmol, 50 fmol, 10 fmol and 1 fmol) of a control oligodeoxyribonucleotide of sequence identical to that of the ligated tag. Lane F: Deposition of tagged single-stranded cDNAs. Approximately 15 fmol of tag are present.

These results demonstrate that the reverse transcription can be performed through the cap and in particular that reverse transcriptase crosses the 5'-P-P-P-5' bond of the cap of eukaryotic messenger RNAs.

FIG. 10 represents the photograph of a 1.5% agarose gel stained with ethidium bromide of the PCR products of the reverse transcription (¹⁄₂₀th of the products of reverse transcription were used for each PCR reaction).

Lanes A and B: molecular weight markers (describe). Lanes C and D: PCR with the globin primers in the presence of cDNA (lane C) or otherwise (lane D). Lanes E and F: PCR with the dehydrogenase primers in the presence of cDNA (lane E) or otherwise (lane F). Lanes G and H: PCR with the pp15 primers in the presence (lane G) or otherwise (lane H) of cDNA. Lanes I and J: PCR with the EIE4 primers in the presence (lane I) or otherwise (lane J) of cDNA.

In lanes C, E, G and I, the presence of a band of the expected size is indicative of the presence of the corresponding sequence in the cDNA population.

FIG. 11 represents the photograph of a 1.5% agarose gel stained with ethidium bromide. Same legend as FIG. 10, but the PCRs were carried out with the anti-sense oligonucleotides of each pair of primers and an oligonucleotide whose sequence corresponds to that of the ligated tag. The amplification products of lanes C and E show that the reverse transcription recopied the RNA molecule and the ligated oligodeoxyribonucleotide tag. The patterns obtained in lane C are probably due to the PCR conditions which were not optimized for the pairs of primers used.

REFERENCES

1. Frohman et al. (1988), PNAS 85, 8998–9002;
2. Delort et al. (1989), NAR 17, 6439–6448;
3. Dumas Milne Edwards et al. (1991), NAR 19, 5227–5232;
4. Frohman-Racine (1993), NAR 21, 1683–1684;
5. Maruyama et Sugano (1993), Gene 138, 171–174;
6. Dumas Milne Edwards (1993): Doctorate thesis, Paris VI, 75–90;
7. Kato and Sekine (1993), EPO-Application: #93921061.3;
8. Sonenberg and Altmann (1989), EPO-Application: #89313030.2;
9. Reddy et al. (1992): Pharmac Ther. Vol. 54, pp. 249–267;
10. Zamecnik et al. (1960), PNAS 46, 811;
11. Agrawal et al. (1986), NAP 14, 6227–6245;
12. O'Shannessy D. J. et al. (1987), Anal. Biochem. 163, 204–209;
13. Ghosh F., EPO-Application No. 89309532.3;
14. Uhlenbeck O. C., Gumport R. J. (1982), T4 RNA Ligase, The Enzymes, V. 15B (P. D. Boyer ed) pp. 31–60. Academic Press;
15. Current Protocol in Molecular Biology. N.Y. 3.15.1. (1994) Ed. John Wiley and Sons, Inc.

We claim:

1. A method for obtaining a polynucleotide comprising the 5' region of an mRNA from a population of mRNAs comprising the steps of:

oxidizing a 2',3'-cis-diol on a cap located at a 5' end of said mRNA to generate a dialdehyde;

coupling said dialdehyde to an amine functional group on a coupling molecule to form a conjugate comprising said coupling molecule and said polynucleotide; and isolating said conjugate from said population of mRNAs.

2. The method of claim 1 further comprising the step of modifying the base at the 3' end of said mRNA or mRNA fragment prior to conducting said oxidizing step such that the base at the 3' end of said mRNA or mRNA fragment lacks an OH group in the 2' and 3' positions.

3. The method of claim 2, wherein said modifying step comprises adding a nucleotide or an oligonucleotide whose 3' end does not comprise a 2',3'-diol functional group to said base at the 3' end of said mRNA or mRNA fragment.

4. The method of claim 3, wherein said modifying step comprises ligating a nucleoside 3',5'-diphosphate (pNp) to said base at the 3' end of said mRNA or mRNA fragment using an enzyme.

5. The method of claim 4, wherein said enzyme comprises RNA ligase.

6. The method of claim 2, wherein said modifying step comprises performing a controlled alkaline hydrolysis on an mRNA or mRNA fragment having a 2',3'-diol functional group on the base at the 3' end of its polyA tail to generate a 3' fragment containing said 2',3'-diol functional group and a 5" fragment containing said cap, said method further comprising the step of separating said 3' fragment from said 5' fragment.

7. The method of claim 1, wherein said oxidizing step comprises performing an oxidation reaction with periodate.

8. The method of claim 1, wherein said coupling step is conducted in an acidic medium and said method further comprises performing a reduction reaction with a borohydride.

9. The method of claim 1, wherein said coupling molecule having an amine functional group thereon comprises a biological molecule.

10. The method of claim 1, wherein said coupling molecule having an amine functional group thereon comprises a labeling molecule.

11. The method of claim 1, wherein said coupling molecule having an amine functional group thereon comprises a molecule which facilitates the isolation of the mRNA or mRNA fragment to which it is coupled.

12. The method of claim 11, wherein said coupling step comprises coupling a coupling molecule to said cap on said mRNA or mRNA fragment to obtain a first conjugate between said coupling molecule and said mRNA or mRNA fragment and the method further comprises the steps of:

contacting said first conjugate with a second molecule, wherein said second molecule binds covalently or non-covalently to said coupling molecule, thereby forming a second conjugate comprising said second molecule, said coupling molecule, and said mRNA or mRNA fragment; and separating said second conjugate from mRNA or mRNA fragments which have not formed said second conjugate.

13. The method of claim 12, further comprising the step of cleaving the bond between said second molecule and said coupling molecule in said second conjugate, thereby releasing said first conjugate.

14. The method of claim 12, wherein said second molecule becomes attached to a solid phase and said separating step comprises separating said solid phase from mRNA or mRNA fragments which have not formed said second conjugate.

15. The method of claim 12, wherein said coupling molecule and said second molecule are biological molecules which associate to form a noncovalent complex.

16. The method of claim 12, wherein said coupling molecule is biotin hydrazide and said second molecule is avidin or streptavidin.

17. The method of claim 13, wherein said solid phase is selected from the group consisting of the inner face of a vessel in which said mRNA or mRNA fragments are present and components which are introduced into said vessel.

18. The method of claim 12, wherein said mRNA comprises a complete mRNA.

19. The method of claim 13 further comprising the step of cleaving said first conjugate between said coupling molecule and said mRNA or mRNA fragment, thereby generating unconjugated mRNA or mRNA fragments.

20. A method for synthesizing a first cDNA strand, comprising:

oxidizing 2',3'-cis-diols on caps located at the 5' ends of polynucleotides comprising mRNAs or mRNA fragments to generate dialdehydes;

coupling said dialdehydes to amine functional groups on coupling molecules to form conjugates comprising said coupling molecules and said polynucleotides;

performing a reverse transcription reaction on said conjugates, thereby forming heteroduplexes comprising a first cDNA strand and said mRNAs or mRNA fragments in said conjugates;

eliminating mRNAs or mRNA fragments which have not formed said heteroduplexes;

capturing said heteroduplexes on a solid phase coated with a second molecule capable of binding to said coupling molecule; and denaturing said heteroduplexes to recover said first cDNA strand.

21. The method of claim 20, wherein said eliminating step comprises performing a digestion with an enzyme which degrades single-stranded or nonhybridized mRNAs or mRNA fragments while leaving said heteroduplexes intact.

22. The method of claim 21, wherein said enzyme is selected from the group consisting of T1 RNase and S1 nuclease.

23. A method for synthesizing double stranded cDNAs corresponding to the 5' ends of polynucleotides comprising mRNAs or mRNA fragments comprising the steps of:

oxidizing 2', 3'-cis-diols on caps located at said 5' ends of said mRNAs or mRNA fragments to generate dialdehydes;

coupling an amine functional group on the 3' end of an oligonucleotide to said dialdehydes at said 5' ends of said mRNAs or mRNA fragments thereby forming oligonucleotide-mRNA conjugates;

performing a reverse transcription reaction on said oligonucleotide mRNA conjugates, thereby generating heteroduplexes comprising first cDNA strands and said oligonucleotide-mRNA conjugates;

denaturing said heteroduplexes;

eliminating single-stranded mRNAs or mRNA fragments; and synthesizing second cDNA strands complementary to said first cDNA strands.

24. An isolated polynucleotide comprising an mRNA-coupling molecule conjugate obtained by the methods of claim 1 or claim 12.

25. A method for obtaining a protein capable of binding to an mRNA comprising the steps of:
    coupling an amine functional group on a coupling molecule to the cap at the 5' end of a polynucleotide comprising an mRNA or mRNA fragment, thereby obtaining a coupling molecule-mRNA conjugate;
    contacting said coupling molecule-mRNA conjugate with a protein capable of recognizing said mRNA or mRNA fragment, thereby forming a complex comprising said protein and said coupling molecule-mRNA conjugate;
    isolating said complex;
    dissociating said protein from said coupling molecule-mRNA complex; and
    recovering said protein.

26. The method of claim 1, wherein said amine functional group is on a molecule which does not naturally bind to said cap.

27. The method of claim 1, further comprising the step of performing a reverse transcription reaction on said polynucleotide comprising the 5' region of an mRNA.

28. The method of claim 1, wherein said coupling molecule is biotin hydrazide.

29. A kit for obtaining a polynucleotide comprising the 5' region of an mRNA from a population of mRNAs comprising:
    an oxidizing reagent for oxidizing a 2',3'-cis-diol on caps located at 5' ends of said mRNA to generate dialdehydes
    a coupling molecule having an amine functional group thereon for forming a conjugate comprising said coupling molecule and said polynucleotide;
    a coupling reagent for coupling said dialdehyde to said amine functional group on said coupling molecule; and
    a modifying reagent for modifying the base at the 3' end of said mRNA or mRNA fragment such that said base at the 3' end of said mRNA or mRNA fragment lacks an OH group in the 2' and 3' positions.

30. The kit of claim 29, wherein said oxidizing reagent is sodium periodate.

31. The kit of claim 29, wherein said coupling reagent comprises an acidic buffer having a pH between 4 and 6 and a borohydride.

32. The kit of claim 29, wherein said modifying reagent comprises a reagent for coupling the 3' end of said mRNA or mRNA fragment to the 5' end of an oligonucleotide or nucleotide, wherein said oligonucleotide or nucleotide does not have a 2',3'-cis-diol at its 3' end.

33. The kit of claim 32, wherein said modifying reagent comprises a nucleotide 3', 5'-diphosphate pNp and a ligation enzyme.

34. The kit of claim 33, wherein said ligation enzyme comprises T4 RNA ligase.

35. A reagent kit for obtaining a polynucleotide comprising the 5' region of an mRNA from a population of mRNAs comprising:
    an oxidizing reagent for oxidizing the 2',3'-cis-diol on a cap located at the 5' end of said mRNA to generate a dialdehyde;
    a coupling molecule having an amine functional group thereon for forming a conjugate comprising said coupling molecule and said polynucleotide;
    a coupling reagent for covalently coupling said dialdehyde to said amine functional group on said coupling molecule; and
    a second molecule which binds covalently or noncovalently to said coupling molecule so as to form a complex or conjugate with said coupling molecule, said second molecule being in solution or attached to a solid phase.

36. The kit of claim 35 further comprising a modifying reagent for modifying the base at the 3' end of said mRNA or mRNA fragment such that said base at the 3' end of said mRNA or mRNA fragment lacks an OH group in the 2' and 3' positions.

37. The kit of claim 29 further comprising reagents for conducting a reverse transcription reaction.

38. The kit of claim 29, wherein said coupling molecule comprises a biological molecule.

39. The kit of claim 29, wherein said coupling molecule comprises biotin hydrazide.

40. The kit of claim 29, wherein said coupling molecule comprises an oligonucleotide having an amine functional group on its 3' end.

41. The kit of claim 29, wherein said coupling molecule is soluble.

* * * * *